US008728452B2

(12) United States Patent
Cannell et al.

(10) Patent No.: US 8,728,452 B2
(45) Date of Patent: May 20, 2014

(54) AQUEOUS FATTY MONOAMINE-CONTAINING SYSTEMS FOR WATER-INSOLUBLE MATERIALS

(75) Inventors: David W. Cannell, Plainfield, NJ (US); Hashimoto Sawa, Westfield, NJ (US); Nghi Van Nguyen, Edison, NJ (US)

(73) Assignee: L'Oreal, Paris (FR)

( * ) Notice: Subject to any disclaimer, the term of this patent is extended or adjusted under 35 U.S.C. 154(b) by 1134 days.

(21) Appl. No.: 11/583,252

(22) Filed: Oct. 19, 2006

(65) Prior Publication Data

US 2008/0095726 A1    Apr. 24, 2008

(51) Int. Cl.
*A61K 8/81*    (2006.01)
(52) U.S. Cl.
USPC .............. 424/70.7; 424/70.27; 424/70.31
(58) Field of Classification Search
None
See application file for complete search history.

(56) References Cited

U.S. PATENT DOCUMENTS

| 4,275,055 | A |   | 6/1981  | Nachtigal et al. |         |
|-----------|---|---|---------|------------------|---------|
| 5,180,584 | A | * | 1/1993  | Sebag et al.     | 510/122 |
| RE40,534  | E | * | 10/2008 | Harrison et al.  | 510/122 |
| 2001/0006652 | A1 | * | 7/2001  | Kahre et al.     | 424/400   |
| 2005/0175568 | A1 | * | 8/2005  | Asari et al.     | 424/70.12 |
| 2006/0286055 | A1 | * | 12/2006 | Cannell et al.   | 424/70.12 |

OTHER PUBLICATIONS

International Cosmetic Ingredient Dictionary, 10th Edition, published by the Cosmetic, Toiletry and Fragrance Association Inc. (CTFA), Washington D.C., USA, 2004.
International Cosmetic Ingredient Dictionary, 7th Edition, published by the Cosmetic, Toiletry and Fragrance Association Inc. (CTFA), Washington D.C., USA), 1997.
McCutcheon's "Detergents and Emulsifiers," North American Edition (1986), published by Allured Publishing Corporation, McCutcheon Division, MC Publishing Co., 175 Rock Road, Glen Rock, NJ 07452 USA, 1986.
McCutcheon's "Functional Materials," North American Edition (1992), McCutcheon Division, MC Publishing Co., 175 Rock Road, Glen Rock, NJ 07452 USA, 1992.

* cited by examiner

*Primary Examiner* — Suzanne Ziska
(74) *Attorney, Agent, or Firm* — Novak Druce Connolly Bove + Quigg LLP

(57) ABSTRACT

The present invention is drawn to an aqueous composition containing: (a) at least one fatty monoamine; (b) at least one nonionic surfactant; (c) at least one compound chosen from an alkyl ether carboxylic acid, an alkyl ether carboxylate, a fatty acid having from about 6 to about 40 carbon atoms, and mixtures thereof; and (d) at least one water-insoluble material, and wherein the composition is homogeneous and clear to substantially clear in appearance.

38 Claims, No Drawings

AQUEOUS FATTY MONOAMINE-CONTAINING SYSTEMS FOR WATER-INSOLUBLE MATERIALS

STATEMENT OF RELATED APPLICATIONS

Not applicable.

BACKGROUND OF THE INVENTION

The present invention relates to a novel aqueous system, based on a combination of at least one fatty monoamine, at least one nonionic surfactant, and at least one compound chosen from an alkyl ether carboxylic acid, an alkyl ether carboxylate, a fatty acid having from about 6 to about 40 carbon atoms, and mixtures thereof, wherein the aqueous system allows water-insoluble materials to be incorporated into aqueous solutions.

Certain water-insoluble ingredients which are oftentimes desirable for the treatment of keratinous substrates are inherently difficult to incorporate into aqueous systems such as shampoos and conditioners without forming a traditional emulsion in either cream or lotion form. Moreover, many of these water-insoluble ingredients suppress lathering which makes the use of aqueous systems such as shampoos and body washes less desirable to consumers. Even in those aqueous systems which do employ these types of water-insoluble ingredients, their presence is minimal due to various performance drawbacks such as poor spreadability, foaming, removal and rinsing or, in the case of styling products, difficulties in removal via shampooing.

Also, when formulating clear aqueous compositions for use in treating keratinous substrates, water-insoluble compounds do not lend themselves to being used therein, due to their inability to significantly associate with the water present in the system.

Thus, there remains a need for a clear aqueous composition which can carry water-insoluble materials while remaining both homogeneous and clear to substantially clear in appearance.

BRIEF SUMMARY OF THE INVENTION

In order to achieve these and other advantages, the present invention is drawn to a composition containing:
  (a) at least one fatty monoamine compound;
  (b) at least one nonionic surfactant;
  (c) at least one compound chosen from an alkyl ether carboxylic acid, an alkyl ether carboxylate, a fatty acid having from about 6 to about 40 carbon atoms, and mixtures thereof; and
  (d) at least one water-insoluble material.

In another embodiment, the present invention is also drawn to a process for treating a keratinous substrate comprising contacting the keratinous substrate with an aqueous composition containing:
  (a) at least one fatty monoamine compound;
  (b) at least one nonionic surfactant;
  (c) at least one compound chosen from an alkyl ether carboxylic acid, an alkyl ether carboxylate, a fatty acid having from about 6 to about 40 carbon atoms, and mixtures thereof; and
  (d) at least one water-insoluble material.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The term "water-insoluble" means those compounds which are either completely or partially insoluble in water. The term "carried" means that the aqueous delivery system containing the water-insoluble ingredients is both homogeneous and clear to substantially clear in appearance.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

The substituent(s) may be further substituted.

"Ethylene oxide group" as defined herein refers to a group of formula —$CH_2CH_2$—O—.

"Propylene oxide group" as defined herein includes groups of formula —$CH_2CH_2CH_2$—O—, groups of formula ($CH_3$)$CHCH_2$—O—, and groups of formula —$CH_2$ ($CH_3$)CH—O—.

"Keratinous substrate" as defined herein may be human keratinous fiber, and may be chosen from, for example, hair, eyelashes, and eyebrows, as well as the stratum corneum of the skin and nails.

"Polymers," as defined herein, include homopolymers and copolymers formed from at least two different types of monomers.

Advantageously, the aqueous composition of the present invention enables water-insoluble materials or ingredients to be carried by the composition and yet provide a clear to substantially clear appearance. Surprisingly, the use of an alcohol is not required in order to render the composition clear to substantially clear in appearance.

The composition of the invention is easy to formulate and gentle on the hair, skin, or eyelashes because the surfactants used therein are generally mild.

The composition of the present invention readily delivers water-insoluble ingredients to the targeted keratinous substrate. Accordingly, this composition can be used in the formulation of hair shampoos, conditioners, deep treatments, hair dyeing compositions, including oxidative dyes and bleaches, permanent waving compositions, curl relaxing compositions, hair setting compositions, bath and body products, sunscreens, cosmetics, skin moisturizers, and the like, all of which are homogeneous and clear to substantially clear in appearance.

The composition can also be used to deliver active water-insoluble pharmaceutical ingredients, particularly in topical applications. Such systems could further help protect against oxidation and rancidity by protecting sensitive ingredients in pharmaceuticals or foods.

The present invention provides for the use of conventional fatty monoamine compounds. Fatty monoamine compounds are those which have more than one hydrocarbon group with from 6 to 22 carbon atoms. Primary, secondary, and tertiary fatty monoamines are useful. Particularly useful are tertiary amido amines having an alkyl group of from about 6 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethyl amine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachnidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, hydroxylated, ethoxylated or propoxylated fatty amines such as ethoxylated stearylamine, dihydroxyethylstearylamine, and arachidylbehenylamine. Useful amines in the present invention are disclosed in U.S. Pat. No. 4,275,055.

In the present invention, the at least one fatty monoamine compound is preferably used in an amount of from greater than 0% to about 30% by weight, preferably from greater than 0% to about 10% by weight, and more preferably from greater than 0% to about 5% by weight, based on the weight of the composition as a whole.

In general, nonionic surfactants having a Hydrophilic-Lipophilic Balance (HLB) of from 8 to 20 are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S).sub.n —O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN° 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from about 10-25, more preferably from about 10-20 moles.

The nonionic surfactant will typically be present in the composition in an amount of from greater than 0% to about 70% by weight, preferably from greater than 0% to 40% by weight, and more preferably from greater than 0% to 20% by weight, based on the weight of the composition as a whole.

The alkyl ether carboxylic acid or alkyl ether carboxylate used in the present invention corresponds to formula I:

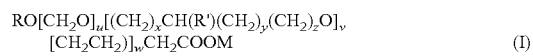

wherein:
R is a hydrocarbon radical containing from 6 to 40 carbon atoms;
u, v and w, independently of one another, represent numbers of from 0 to 60;
x, y and z, independently of one another, represent numbers of from 0 to 13;
R' represents hydrogen, alkyl, the sum of x+y+z being≥0;
M is an alkali metal or alkaline earth metal (i.e., ether carboxylate) or hydrogen (i.e., ether carboxylic acid).

Ether carboxylic acids or carboxylates corresponding to formula (I) can be obtained by alkoxylation of alcohols ROH with ethylene oxide as sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (I), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group;

u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8;

M may be chosen from lithium, sodium, potassium, calcium, magnesium or hydrogen.

Suitable ether carboxylic acids or ether carboxylates include, but are not limited to, the following representatives referred to by their INCI names (INCI: nomenclature for raw materials according to the International Cosmetic Ingredient Dictionary, 7th Edition, published by the Cosmetic, Toiletry and Fragrance Association Inc. (CTFA), Washington D.C., USA): Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_9$-$C_{11}$, Pareth-6 Carboxylic Acid, $C_{11}$-$C_{15}$ Pareth-7 Carboxylic Acid, $C_{12}$-$C_{13}$ Pareth-5 Carboxylic Acid, $C_{12}$-$C_{13}$ Pareth-8 Carboxylic Acid, $C_{12}$-$C_{13}$ Pareth-12 Carboxylic Acid, $C_{12}$-$C_{15}$ Pareth-7 Carboxylic Acid, $C_{12}$-$C_{15}$ Pareth-8 Carboxylic Acid, $C_{14}$-$C_{15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Magnesium Laureth-11

Carboxylate, Sodium-PPG-6-Laureth-6-Carboxylate, Sodium PPG-8-Steareth-7 Carboxylate, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Sodium Capryleth-2 Carboxylate, Sodium Capryleth-9 Carboxylate, Sodium Ceteth-13 Carboxylate, Sodium $C_9$-$C_{11}$, Pareth-6 Carboxylate, Sodium $C_{11}$-$C_{15}$ Pareth-7 Carboxylate, Sodium $C_{12}$-$C_{13}$ Pareth-5 Carboxylate, Sodium $C_{12}$-$C_{13}$ Pareth-8 Carboxylate, Sodium $C_{12}$-$C_{13}$ Pareth-12 Carboxylate, Sodium $C_{12}$-$C_{15}$ Pareth-6 Carboxylate, Sodium $C_{12}$-$C_{15}$ Pareth-7 Carboxylate, Sodium $C_{12}$-$C_{15}$ Pareth-8 Carboxylate, Sodium $C_{14}$-$C_{15}$ Pareth-8 Carboxylate, Sodium Deceth-2 Carboxylate, Sodium Hexeth4 Carboxylate, Sodium Isosteareth-6 Carboxylate, Sodium Isosteareth-11 Carboxylate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate Sodium Laureth-11 Carboxylate, Sodium Laureth-12 Carboxylate, Sodium Laureth-13 Carboxylate, Sodium Laureth-14 Carboxylate, Sodium-Laureth-17 Carboxylate, Sodium-Trudeceth-3 Carboxylate, Sodium Trideceth-6 Carboxylate, Sodium Trideceth-7 Carboxylate, Sodium Trideceth-8 Carboxylate, Sodium Trideceth-12 Carboxylate, Sodium Undeceth-5 Carboxylate, Trideceth-3 Carboxylic Acid, Trideceth4 Carboxylic Acid, Trideceth-7 Carboxylic acid, Trideceth-15 Carboxylic Acid, Trideceth-19 Carboxylic Acid, Undeceth-5 Carboxylic Acid.

Particularly preferred are oleth-10 carboxylic acid, laureth-5 carboxylic acid, and laureth-11 carboxylic acid. The fatty acid having from about 6 to about 40 carbon atoms that may also be used in the present invention corresponds to formula II:

$$R''COOH \quad (II)$$

wherein:
R" is a hydrocarbon radical containing from 6 to 40 carbon atoms. In addition, R" is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group.

Suitable fatty acids having from about 6 to about 40 carbon atoms include, but are not limited to the following representatives referred to by their INCI names (INCI: nomenclature for raw materials according to the International Cosmetic Ingredient Dictionary, 10th Edition, published by the Cosmetic, Toiletry and Fragrance Association Inc. (CTFA), Washington D.C., USA): Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Tallow Acid, Undecanoic Acid, Undecylenic Acid, Wheat Germ Acid.

Particularly preferred fatty acids having from about 6 to about 40 carbon atoms include Capric Acid, Caprylic Acid, Lauric Acid, Linoleic Acid, Oleic Acid, Isostearic Acid, and Stearic Acid.

The alkyl ether carboxylic acid and/or alkyl ether carboxylate and/or fatty acid having from about 6 to about 40 carbon atoms is present in the composition in an amount ranging from greater than 0 to about 50% by weight, preferably from greater than 0 to about 30% by weight, and more preferably from greater than 0 to about 15% by weight, based on the weight of the composition as a whole.

It has surprisingly been found that by combining at least one fatty monoamine compound, at least one nonionic surfactant, at least one alkyl ether carboxylic acid/alkyl ether carboxylate/fatty acid, having from about 6 to about 40 carbon atoms and at least one water-insoluble material, in a certain ratio by weight relative to each other, a homogeneous and clear to substantially clear aqueous composition can be formed capable of carrying up to about 50% by weight, preferably up to about 30% by weight, more preferably up to about 20% by weight, and most preferably up to about 10% by weight, all weights being based on the weight of the composition, of water-insoluble ingredients. The precise ratio by weight of fatty monoamine compound:nonionic surfactant:alkyl ether carboxylic acid/alkyl ether carboxylate/fatty acid having from about 6 to about 40 carbon atoms: water-insoluble material necessary to make a clear to substantially clear composition will depend on the specific compounds chosen and, once chosen, can be determined by those of ordinary skill in the art.

Water-insoluble materials or ingredients include, but are not limited to, the following:

(1) Lipophilic "ingredients" or "materials" such as silicones, oil-soluble vitamins such as Vitamin E and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, aminosilicone and laurylmethicone copolyol. The lipophilic ingredients will, for example, moisturize or condition the skin, hair, and/or eyelashes and leave behind no oily feel.

(2) Water-insoluble polymers, resins, and latexes, wherein the polymers and resins include but are not limited to those containing carboxyl moieties, such as acrylates and other carboxy polymers.

Preferred water-insoluble ingredients for use in the present invention include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes.

The composition can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

The process for making the composition involves introducing at least one fatty monoamine compound, at least one nonionic surfactant, at least one alkyl ether carboxylic acid or alkyl ether carboxylate or fatty acid, having from about 6 to about 40 carbon atoms, and at least one water-insoluble ingredient to an aqueous solution to form a diluted mixture. Heat may be optionally introduced at any stage of the preparation of the mixture and the final diluted mixture is allowed to cool. Preferably, the aqueous delivery system obtained can carry a high load (i.e., 50% is considered a high load) of the water-insoluble ingredient.

Another embodiment of the present invention is drawn to a process for treating a keratinous substrate comprising contacting the keratinous substrate with an aqueous composition containing (a) at least one fatty monoamine compound;

(b) at least one nonionic surfactant;

(c) at least one compound chosen from an alkyl ether carboxylic acid, an alkyl ether carboxylate, a fatty acid having from about 6 to about 40 carbon atoms, and mixtures thereof; and (d) at least one water-insoluble material.

The keratinous substrate includes, but is not limited to, hair, skin, or eyelashes. The term treating in the context of this invention includes, but is not limited to, shampooing, conditioning, dyeing, bleaching, permanent waving, relaxing, setting, moisturizing, and making-up, for example, applying mascara or foundation.

As mentioned previously, the composition may be in the form of shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions.

The composition may further contain proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the keratinous substrate. Cationic proteins or proteins in general may be stabilizers for the aqueous delivery system and enhance its delivery by changing the charge of the aqueous delivery system. The skin and the hair attract cationic ingredients, and proteins are generally substantive to these tissues.

Other optional ingredients include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

The invention will be further clarified by the following examples, which are intended to be illustrative of the invention, but not limiting thereof.

EXAMPLES

General Procedure: Heat water to 80° C. and add all of the ingredients and mix well until uniform. Cool to RT, pour at 60° C. if necessary.

Example 1

The following mixtures A-G (in grams weight) were made using the General Procedure.

|  | A | B | C | D | E | F | G |
|---|---|---|---|---|---|---|---|
| D.I. Water | 57.2 | 57.2 | 57.2 | 57.2 | 57.2 | 57.2 | 57.2 |
| Lexamine S-13 (stearamidopropyldimethylamine) | 2 | 0 | 2 | 2 | 0 | 2 | 0 |
| Procetyl AWS (PPG-5 Ceteth-10) | 25.5 | 25.5 | 0 | 25.5 | 25.5 | 0 | 0 |
| Laureth-11 Carboxylic Acid | 11.2 | 11.2 | 11.2 | 0 | 0 | 0 | 11.2 |
| Olive Oil | 4.1 | 4.1 | 4.1 | 4.1 | 4.1 | 4.1 | 4.1 |
| Clarity | clear | hazy | hazy | hazy | hazy | hazy | hazy |
| Dilutions | clear | hazy | hazy | hazy | hazy | hazy | hazy |

The complete system, as shown in column A, is a clear system. It remains clear when diluted with water indefinitely. If one or two ingredients from the ANCA mixture (amine, nonionic, alkyl ether carboxylic acid mixture) are removed from the formula, as shown in columns B-G, the mixtures are no longer clear; they are hazy and remain hazy when diluted with water.

This example illustrates the necessity of having all three components (A, N, and CA) in order for the system to carry olive oil, and to still remain clear upon dilution with water.

Example 2

The following ANCA systems with vegetable oils were made using the General Procedure. All of the formulas below have been Q.S. to 100% with D.I. water. These systems contain Stearamidopropyldimethylamine (Lexamine S-13), Non-ionic (Procetyl AWS), Alkyl Ether Carboxylic Acid (Oleth-10 Carboxylic Acid, Laureth-5 Carboxylic Acid, and Laureth-11 Carboxylic Acid) and oils (Olive oil, Avocado oil).

| Amine | Non-ionic | Carboxylic Acid | Vegetable Oil |
|---|---|---|---|
| Lexamine S-13 (2%) | Procetyl AWS (30%) | Oleth-10 Carboxylic Acid (1%) | Olive Oil (4%) |
| Lexamine S-13 (2%) | Procetyl AWS (30%) | Laureth-5 Carboxylic Acid (1%) | Olive Oil (4%) |
| Lexamine S-13 (2%) | Procetyl AWS (30%) | Laureth-11 Carboxylic Acid (1%) | Olive Oil (3%) |
| Lexamine S-13 (2%) | Procetyl AWS (30%) | Oleth-10 Carboxylic Acid (1%) | Avocado Oil (4%) |
| Lexamine S-13 (2%) | Procetyl AWS (30%) | Laureth-5 Carboxylic Acid (1%) | Avocado Oil (4%) |
| Lexamine S-13 (2%) | Procetyl AWS (30%) | Laureth-11 Carboxylic Acid (1%) | Avocado Oil (4%) |

These systems are clear, and remain clear when diluted with water indefinitely.

Example 3

The following ANCA systems with silicones were made using the General Procedure. All of the formulas below have been Q.S. to 100% with D.I. water. These systems contain Stearamidopropyldimethylamine (Lexamine S-13), Non-ionic (Procetyl AWS), Alkyl Ether Carboxylic Acid (Oleth-10 Carboxylic Acid, Laureth-5 Carboxylic Acid, and Laureth-11 Carboxylic Acid) and silicone (Phenyltrimethicone).

| Amine | Non-ionic | Carboxylic Acid | Silicone |
|---|---|---|---|
| Lexamine S-13 (1%) | Procetyl AWS (30%) | Laureth-5 Carboxylic Acid (1%) | Phenyltrimethicone (4%) |
| Lexamine S-13 (1%) | Procetyl AWS (30%) | Laureth-11 Carboxylic Acid (1%) | Phenyltrimethicone (4%) |

These systems are clear, and remain clear when diluted with water indefinitely.

Example 4

The following ANCA systems with waxes were made using the General Procedure. All of the formulas below have been Q.S. to 100% with D.I. water. These systems contain Stearamidopropyldimethylamine (Lexamine S-13), Non-ionic (Procetyl AWS), Alkyl Ether Carboxylic Acid (Oleth-10 Carboxylic Acid, Laureth-5 Carboxylic Acid, and Laureth-11 Carboxylic Acid) and wax (Phytowax Olive).

| Amine | Non-ionic | Carboxylic Acid | Wax |
|---|---|---|---|
| Lexamine S-13 (1%) | Procetyl AWS (30%) | Laureth-5 Carboxylic Acid (1%) | Phytowax Olive (4%) |
| Lexamine S-13 (1%) | Procetyl AWS (30%) | Laureth-11 Carboxylic Acid (1%) | Phytowax Olive (4%) |

These systems are clear, and remain clear when diluted with water indefinitely.

Example 5

The following ANCA systems with hydrocarbons were made using the General Procedure. All of the formulas below have been Q.S. to 100% with D.I. water. These systems contain Stearamidopropyldimethylamine (Lexamine S-13), Non-ionic (Procetyl AWS), Alkyl Ether Carboxylates (Oleth-10 Carboxylic Acid, Laureth-5 Carboxylic Acid, and Laureth-11 Carboxylic Acid) and hydrocarbon (Mineral Oil).

| Amine | Non-ionic | Carboxylic Acid | Hydrocarbon |
|---|---|---|---|
| Lexamine S-13 (2%) | Procetyl AWS (25%) | Oleth-10 Carboxylic Acid (1%) | Mineral Oil (4%) |
| Lexamine S-13 (2%) | Procetyl AWS (25%) | Laureth-5 Carboxylic Acid (1%) | Mineral Oil (4%) |
| Lexamine S-13 (2%) | Procetyl AWS (25%) | Laureth-11 Carboxylic Acid (1%) | Mineral Oil (4%) |

These systems are clear, and remain clear when diluted with water indefinitely.

Example 6

The following opaque ANCA system that contains Amine (Lexamine S-13), Non-ionic (Procetyl AWS), Alkyl Ether Carboxylate (Laureth-11 Carboxylic Acid) and Olive Oil was made using the General Procedure:

| | |
|---|---|
| DI Water | 67.70% |
| Lexamine S-13 | 1.50% |
| Laureth-11 Carboxylic Acid | 0.80% |
| Procetyl AWS | 25.00% |
| Olive Oil | 5.00% |

Example 7

The following clear ANCA system that contains Amine (Lexamine S-13), Non-ionic (Procetyl AWS), Fatty Acid (Oleic Acid) and Mineral Oil was made using the General Procedure:

| | |
|---|---|
| DI Water | 66.33% |
| Lexamine S-13 | 0.49% |
| Oleic Acid | 1.75% |
| Procetyl AWS | 26.19% |
| Mineral Oil | 5.24% |

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. An aqueous composition comprising:
   (a) greater than 0 to 30% by weight of at least one fatty monoamine compound;
   (b) greater than 0 to 70% by weight of at least one nonionic surfactant;
   (c) greater than 0 to 50% by weight of at least one compound chosen from an alkyl ether carboxylic acid, an alkyl ether carboxylate, and a fatty acid having from about 6 to about 40 carbon atoms; and
   (d) at least 3 to 50% by weight of at least one water-insoluble material selected from the group consisting of natural-oils, synthetic oils, hydrocarbons, and waxes; wherein the aqueous composition is clear in appearance and does not include silicones.

2. The composition of claim 1 wherein (a) is a tertiary amido amine having an alkyl group with from about 12 to about 22 carbon atoms.

3. The composition of claim 1 wherein (a) is present in an amount greater than 0 to about 5% by weight, based on the weight of the composition.

4. The composition of claim 1 wherein (b) has an HLB of at least about 8.

5. The composition of claim 1 wherein (b) is present in an amount greater than 0 to about 20% by weight, based on the weight of the composition.

6. The composition of claim 1 wherein (c) is an alkyl ether carboxylic acid.

7. The composition of claim 1 wherein (c) is a laureth-5 carboxylic acid.

8. The composition of claim 1 wherein (c) is an oleth-10 carboxylic acid.

9. The composition of claim 1 wherein (c) is a laureth-11 carboxylic acid.

10. The composition in claim 1 wherein (c) is a fatty acid having from about 6 to about 40 carbon atoms.

11. The composition in claim 1 wherein (c) is Oleic Acid.

12. The composition in claim 1 wherein (c) is Stearic Acid.

13. The composition of claim 1 wherein (c) is present in an amount greater than 0 to about 15% by weight, based on the weight of the composition.

14. The composition of claim 1 wherein (d) is present in an amount of at least 3 to about 10% by weight, based on the weight of the composition.

15. The composition of claim 1 wherein (d) is a natural oil.

16. A process for treating a keratinous substrate comprising contacting the keratinous substrate with an aqueous composition of claim 1.

17. The process of claim 16 wherein (a) is a tertiary amido amine having an alkyl group with from about 12 to about 22 carbon atoms.

18. The process of claim 16 wherein (a) is present in an amount greater than 0 to about 30% by weight, based on the weight of the composition.

19. The process of claim 16 wherein (a) is present in an amount greater than 0 to about 5% by weight, based on the weight of the composition.

20. The process of claim 16 wherein (b) has an HLB of at least about 8.

21. The process of claim 16 wherein (b) is present in an amount greater than 0 to about 70% by weight, based on the weight of the composition.

22. The process of claim 16 wherein (b) is present in an amount greater than 0 to about 20% by weight, based on the weight of the composition.

23. The process of claim 16 wherein (c) is an alkyl ether carboxylic acid.

24. The process of claim 16 wherein (c) is a laureth-5 carboxylic acid.

25. The process of claim 16 wherein (c) is an oleth-10 carboxylic acid.

26. The process of claim 16 wherein (c) is a laureth-11 carboxylic acid.

27. The process of claim 16 wherein (c) is a fatty acid having from about 6 to about 40 carbon atoms.

28. The process of claim 16 wherein (c) is Oleic Acid.

29. The process of claim 16 wherein (c) is Stearic Acid.

30. The process of claim 16 wherein (c) is present in an amount greater than 0 to about 50% by weight, based on the weight of the composition.

31. The process of claim 16 wherein (c) is present in an amount greater than 0 to about 15% by weight, based on the weight of the composition.

32. The process of claim 16 wherein (d) is present in an amount of at least 3 to about 50% by weight, based on the weight of the composition.

33. The process of claim 16 wherein (d) is present in an amount of at least 3 to about 10% by weight, based on the weight of the composition.

34. The process of claim 16 wherein (d) is a natural-oil.

35. The process of claim 16 wherein the keratinous substrate is hair.

36. A personal care composition comprising the composition of claim 1.

37. An aqueous composition comprising:
   (a) greater than 0 to 5% by weight of a tertiary amido amine having an alkyl group with from 12 to 22 carbon atoms;
   (b) greater than 0 to 40% by weight of an alkoxylated derivative of a fatty alcohol;
   (c) greater than 0 to 30% by weight at least one compound chosen from an alkyl ether carboxylic acid; and
   (d) at least 3 to about 50% by weight of a water-insoluble material selected from the group consisting of a natural-oil, a synthetic oil, a hydrocarbon, and a wax; wherein the aqueous composition clear in appearance and does not include silicones.

38. The aqueous composition according to claim 37, wherein the composition is homogenous and clear without requiring the use of an alcohol.

* * * * *